United States Patent [19]

Hoang et al.

[11] Patent Number: 5,607,699
[45] Date of Patent: Mar. 4, 1997

[54] NON-AQUEOUS EMOLLIENT IODOPHOR FORMULATIONS

[75] Inventors: Minh Q. Hoang, Taylorsville; Mohammad A. Khan, Sandy, both of Utah

[73] Assignee: Becton Dickinson and Company, Franklin Lakes, N.J.

[21] Appl. No.: 440,288

[22] Filed: May 12, 1995

[51] Int. Cl.⁶ .......................... A61K 33/36; A61K 31/355
[52] U.S. Cl. .................. 424/672; 424/667; 424/669; 424/671; 514/458
[58] Field of Search ..................... 424/405, 667, 424/669, 671, 672; 514/458

[56] References Cited

U.S. PATENT DOCUMENTS

| | | | |
|---|---|---|---|
| 3,235,446 | 2/1966 | Shelanski et al. | 167/17 |
| 4,017,407 | 4/1977 | Cantor et al. | 252/106 |
| 4,271,149 | 6/1981 | Winicov et al. | 424/150 |
| 4,867,897 | 9/1989 | Kolstad | 252/106 |
| 4,873,354 | 10/1989 | Globus | 558/51 |
| 5,000,749 | 3/1991 | LeVeen et al. | 604/904 |
| 5,116,623 | 5/1992 | Khan et al. | 424/616 |
| 5,180,061 | 1/1993 | Khan et al. | 206/570 |
| 5,439,681 | 8/1995 | Khan et al. | 424/400 |

Primary Examiner—Kevin E. Weddington
Attorney, Agent, or Firm—Nanette S. Thomas; Bruce S. Weintraub

[57] ABSTRACT

Non-aqueous emollient iodophor formulations for use as a skin washing agents, comprising non-ionic surfactants, coconut oil, mineral oil, iodine, sodium iodide and an organic base solvent. The non-aqueous formulations substantially do not irritate the skin and will provide antimicrobial effectiveness to the skin.

3 Claims, No Drawings

NON-AQUEOUS EMIOLLIENT IODOPHOR FORMULATIONS

BACKGROUND OF THE INVENTION

1. Field of the Invention

This invention relates to emollient iodophor formulations and more particularly to non-aqueous emollient iodophor formulations that are particularly useful in the healthcare profession.

2. Description of Related Art

Hand washing by healthcare professionals is an essential component of infection control activities. Healthcare professionals attending to patient care wash their hands to control the spread of infection from patient to patient. Surgical procedures are routinely proceeded by surgical hand scrubbing and patient pre-operative skin prepping.

Hand washing procedures are performed in several ways. Several procedures include products such as an ordinary antimicrobial bar soap, a skin disinfecting or pre-operative prepping agent or rubbing alcohol. Such procedures and products contain antimicrobial agents such as iodine, chlorhexidine gluconate, para-chlorometa-xylenol and hexachlorophenes. The use of these procedures and products repeatedly is hard and rough on skin.

An alcohol solution containing a tincture of iodine, is also recognized to be an effective disinfecting agent. Tincture of Iodine USP contains from about 1.8% to about 2.2% iodine in 50% ethyl alcohol, 50% water and about 2.1% to about 2.6% of sodium iodide. This particular solution causes irritation to the skin and a routine application of this solution for disinfection may cause burn to the skin. To avoid such irritation, organic complexing agents such as polyvinylpyrrolidone (PVP), surfactants and starches are used in the solution to complex with the iodine to release iodine on demand thereby reducing the risk of irritation and iodine burn on the skin. The organic-iodine complexes are known as iodophors. Most iodine containing surgical scrubs and preps are formulated by using PVP and surfactant iodine complexed iodophors.

Various publications disclose iodophor compositions. Such publications include U.S. Pat. Nos. 3,235,446; 4,017,407; 4,873,354; 4,271,149; 4,113,857; 4,597,975; 5,000,749 and 5,180,061.

Since iodine is a known irritant to the skin and some persons are sensitive to iodine, repeated application of products containing iodine to the skin is not desirable. Irritation includes rashes, dryness and redness. Since the tolerance of such products containing iodine is low, formulations such as antimicrobial soaps and alcohol scrubs comprising hexachlorophene and chlorhexidine gluconate may be used instead. However, due to the broad spectrum of disinfecting properties of iodophor compositions, there is a need for an emollient iodophor surgical scrub to provide protection to the skin from the harsh attack of iodine.

SUMMARY OF THE INVENTION

The present invention is an iodophor formulation that provides antimicrobial effectiveness and is mild and gentle to human skin. The iodophor formulation desirably comprises:

(a) non-ionic surfactants;
(b) iodine;
(c) sodium iodide;
(d) coconut oil diethanolamine condensate;
(e) a surfactant compatible with hydrophobic materials;
(f) mineral oil;
(g) an emulsifier;
(h) an alkylaryl sulfonate;
(i) an emollient and/or moisturizer; and
(j) an organic base solvent.

Preferably, the iodophor formulation may further comprise fragrances and antioxidants. Antioxidants prevent degredation of materials by oxidation.

Most preferably, the iodophor formulations of the present invention are not aqueous.

Most preferably, the iodophor formulations comprise by weight:

(a) from about 20% to about 40% of nonionic surfactants;
(b) from about 0.5% to about 2.5% of iodine crystals;
(c) from about 0.5% to about 2.0% of sodium iodide;
(d) from about 0.5% to about 2.0% of coconut oil diethanolamine condensate;
(e) from about 5.0% to about 15.0% of a surfactant compatible with hydrophobic materials;
(f) from about 1.0% to about 5.0% of a mineral oil;
(g) from about 1.0% to about 5.0% of an emulsifier,
(h) from about 1.0% to about 5.0% of an alkylaryl sulfonate,
(i) from about 0.1% to about 5.0% of an emollient and/or moisturizer; and
(j) from about 18.5% to about 70.4% of an organic base solvent.

Preferably, the iodophor formulations may further comprise (k) from about 0.1% to about 1.0% of a fragrance; and
(l) from about 0.1% to about 1.0% of vitamin E.

The iodophor formulations of the present invention are useful in providing substantial antimicrobial effectiveness to the skin in view of the iodophor component of the formulation and non-irritancy to the skin in view of the mineral oil and emollients of the formulation.

Attributes of the formulations of the present invention include its ability to not dry the skin and its use in the healthcare profession. Most notably, the formulations of the present invention do not contain water, and therefore, the stability of the formulations is considerably enhanced. This is due to the fact that the iodine is more stable in organic solvents than in water solutions. In water solutions, iodine changes to hydroiodic acid. Thus, the pH of a water based formulation becomes acidic causing more irritation to the skin.

The formulations of the present invention substantially minimize the corrosive attack of iodine on the skin because the formulations provide the skin with complexed iodine and oil to minimize chapping and dryness of the skin as well as emolliency to soothe and comfort the skin.

Most importantly, since the formulations are soluble in water, scrubbing can be done after mixing the formulation with water and finally washing the hands with water to have clean hands before donning into gloves. The emollients left on the skin will provide comfort to the skin and reduce irritation due to the iodine.

An advantage of the formulations of the present invention is that they provide substantial bactericidal effectiveness. In particular, they provide bactericidal effectiveness with respect to *Staphylococcus aureus, Candida albicans, Pseudomonas aeruginosa, Escherichia coli,* and the like.

Further advantages of the formulations of the present invention is that they have significant foaming properties, good solubility in water and adequate detergency.

A further advantage of the formulations is that the components of the formulations do not readily penetrate or are not readily absorbed by the skin.

Another advantage of the formulations of the present invention is that shelf life of a product using the formulations of the present invention is maximized and the formulations of the present invention may be packaged in plastic.

Most surgical scrub solutions are water based. Therefore, the solvent for these solutions is water which constitutes a major fraction of the formulation. Since these products may not be used immediately, the packaged product loses water moisture slowly until it dries due to the normal aging process. The users, therefore, have to reconstitute the solution by wetting the sponge with water and squeezing the foam several times before using the product for scrubbing and washing the hands. This causes considerable inconvenience to the health care professionals.

However, when the formulations of the present invention are impregnated in a sponge, concerns regarding moisture loss through the package are substantially eliminated because there is no water to start with. The impregnated sponge, therefore, remains moist and not dry, and, when used as usual, will not cause any inconvenience to the users.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The iodophor formulations of the present invention comprise:

(a) nonionic surfactants;

(b) iodine;

(c) sodium iodide;

(d) coconut oil diethanolamine condensate;

(e) a surfactant compatible with hydrophobic materials;

(f) mineral oil;

(g) an emulsifier;

(h) an alkylaryl sulfonate;

(i) an emollient or moisturizer; and (j) an organic solvent base.

The iodophor formulations may further comprise fragrances and an antioxidant such as vitamin E.

Desirably, the pH of the formulations are from about 2.0 to about 5.0, preferably from about 2.5 to about 3.5 and most preferably from about 2.9 to about 3.1.

Nonionic surfactants may be used in the formulations of the present invention to complex iodine so as to reduce irritation to human skin. Most desirably, the nonionic surfactants used in the formulations of the present invention produce good foam, are good surface active agents, have low toxicity and have the ability to complex iodine.

Nonionic surfactants for use in the formulations of the present invention include, but is not limited to, poly(oxypropylene)poly(oxyethylene) condensates or polyols containing about 50% to about 70% ethylene oxide and nonylphenoxypoly(ethyleneoxy)ethanol and octylphenoxypoly(ethyleneoxy)ethanol.

The most suitable non-ionic surfactants for the formulations of the present invention are the PLURONIC® series of polyoxyethylene polyoxypropylene polyols (trademark of BASF Corporation, Parsippany, N.J.) and the IGEPAL® series of alkylphenoxypolyoxy-ethylene alcohols (a trademark of GAF Corp., Wayne, N.J.). A single nonionic surfactant or a mixture may be used.

Preferably, a PLURONIC polyol may be present in the formulations in an amount from about 10 to about 20 weight percent, and most preferably at about 15 weight percent.

Preferably, an IGEPAL surfactant may be present in the formulations in an amount from about 10 to about 20 weight percent, and most preferably at about 13 weight percent.

Iodine is used in the formulations of the present invention as an antimicrobial agent. Most desirably, iodine is used in the formulations of the present invention to disinfect the skin. Iodine will complex with the organic carrier.

Iodine for use in the formulations of the present invention include, but is not limited to, elemental iodine in the crystalline form and polyvinyl pyrrolidone iodine.

Preferably, iodine may be present in the formulations in the amount from about 0.5 to about 2.5 weight percent, and most preferably at about 1.65 weight percent.

Sodium iodide may be used in the formulations of the present invention to aid and stabilize the complex formation and to reduce the iodine vapor pressure by reducing the free iodine concentration.

Potassium iodide may be used in the formulations of the present invention instead of sodium iodide.

Preferably, sodium iodide may be present in the formulations in an amount from about 0.5 to about 2.0 weight percent, and most preferably at about 1.0 weight percent.

A coconut oil diethanolamine condensate is preferably used in the formulations because it is an adjuvant for surfactants and stabilizes the foam. Since surfactants foam in water, by using coconut oil, the foam is stabilized.

A commercially available coconut oil diethanolamine condensate is GAFAMIDE CDD-518 (a trademark of GAF Corp., Wayne, N.J.).

Preferably, the coconut oil diethanolamine condensate is present in the formulations in an amount from about 0.5 to about 2.0 weight percent and most preferably at about 0.7 weight percent.

A mineral oil may be used in the formulations to prevent dryness to human skin. In particular, white mineral oils are commonly used as a skin oil substitute on dry and chapped hands.

A mineral oil may be used in the formulations in an amount from about 1.0 to about 5.0 weight percent and most preferably at about 2.0 weight percent.

A surfactant compatible with hydrophobic materials for use in the formulation of the present invention includes polyoxyethylene 4 lauryl ether. Since emollients such as mineral oils are hydrophobic this surfactant helps to keep the mineral oil in the formulation.

A suitable surfactant compatible with hydrophobic materials is Brij 30 (trademark of ICI America, Wilmington, Del.).

Preferably, the surfactant is present in the formulations in the amount from about 5.0 to about 15.0 and most preferably at about 9.0 weight percent.

An emulsifier is used in the formulations to disperse oily emollients in water solution. Most importantly, an emulsifier is a solubilizer.

A suitable emulsifier for the formulations is an ethoxylated (75 moles) lanolin, Solulan® 75 (trademark of Amerchol Corporation, Edison, N.J.) (CTFA adopted name is PEG-75 lanolin).

Preferably, an emulsifier is present in the formulations in an amount from about 1.0 to about 5.0 weight percent and most preferably at about 4.0 weight percent.

An alkylaryl sulfonate may be used in the formulations of the present invention to provide good detergency, foaming and emulsifying properties to the formulations. Preferably, an alkylaryl sulfonate is used in the formulation in an amount from about 1.0 to about 5.0 weight percent and most preferably about 3.0 weight percent.

A suitable organic solvent may be used in the formulations as a carrier. The suitable solvent must be miscible with water and must be an excellent base solvent. The suitable solvent substantially allows the formulation to be used with water as a disinfectant and as a detergent.

A preferable organic solvent is propylene glycol. Not only is propylene glycol an excellent base, but it functions as a skin emollient and provides the formulations with a soothing and comfortable feeling to human skin.

A polyalkylene glycol is used in the formulations to serve as a skin oil substitute. A polyalkylene glycol is a synthetic oily substance and is typically characterized as a skin conditioner. The selection of a polyalkylene glycol is based on its biocompatibility and its ability to protect the skin from drying and chapping.

Other ingredients which are conventional or desirable for aesthetic purposes may also be added to the formulations as long as they do not adversely affect the overall properties of the formulations. Such ingredients may include polyvinyl pyrrolidone, commercially available as KOLLIDON® (tradename of BASF Wyandoth Corporation, Parsippany, N.J.).

If desired, the formulations of the present invention may include a perfume or fragrance to provide a pleasing scent or a dye to provide a characteristic color.

If desired, the formulations of the present invention may also include antioxidants such as vitamin E.

The formulations of the present invention are prepared by mixing all the ingredients together and agitating by stirring until the iodine crystals are dissolved to form a clear solution. The solution is warmed while stirring to speed up the dissolution of the iodine. After cooling to room temperature, the pH of the solution is adjusted to a desired pH.

Adjustment of the pH of the formulations is desirable so that they are compatible with the pH of the skin and to avoid unnecessary irritation to the skin. Small amounts, less than about 1% of a nontoxic acidic substance may be added to the formulations.

Suitable non-toxic acids include hydrochloric acid, sulfuric acid, phosphoric acid, citric acid, lactic acid and gluconic acid.

The formulations may be adjusted to a pH within the range from about 2 to about 5. Most preferably, the pH is within the range of about 2.0 to about 3.5.

Generally, the formulations of the present invention may be in liquid form but may also be in the form of a gel or ointment.

The formulations of the present invention may be used in conjunction with a polyurethane foam sponge in a surgical scrub. The sponge may of course be used for germicidal cleansing by itself, but preferably is used in conjunction with a handle in a scrub unit. In this embodiment, the sponge may be conventionally affixed to a plastic, preferably polyethylene handle. The handle may also carry bristles as an aid in scrubbing. The sponge loaded with the formulation of the present invention or preferably the scrub unit, may be included in a plastic package for surgical scrubbing.

The sponge may be a polyurethane foam, synthesized from a polyisocyanate, a polyglycol, a chain extender, and a blowing agent. The sponge may be a polyester polyurethane or a polyether polyurethane type.

Typical surgical scrub assemblies include the E-Z SCRUB® Surgical Scrub Systems (a trademark of Becton, Dickinson and Company, Franklin Lakes, N.J.).

Various other modifications will be apparent to and may be readily made by those skilled in the art without departing from the scope and spirit of the invention.

The following examples are not limited to any specific embodiment of the invention, but are only exemplary.

EXAMPLE 1

PREPARATION OF A NON-AQUEOUS IODOPHOR FORMULATION

The iodopher formulation of the present invention was prepared with the following ingredients:

| Ingredients | Weight Percent |
| --- | --- |
| Non-Ionic Surfactants | 28.0 |
| Iodine Crystals | 1.65 |
| Sodium Iodide | 1.0 |
| Compatible Surfactant | 9.0 |
| Coconut Oil Diethanolamine Condensate | 0.70 |
| Mineral Oil | 2.0 |
| Emulsifier | 4.0 |
| Aloe Vera | 1.0 |
| Alkylaryl Sulfonate | 3.0 |
| Organic Solvent | 49.65 |

In a mixing vessel, all of the above ingredients were mixed together and agitated by stirring until the iodine crystals dissolved to form a clear solution. The solution was warmed while being stirred to speed up the dissolution of the iodine. The solution was then cooled to room temperature. The pH of the solution was then adjusted with a sufficient amount of 6N hydrochloric acid to adjust the pH from about 2 to about 5.

EXAMPLE 2

BACTERICIDAL EFFECTIVENESS EVALUATION OF NON-AQUEOUS IODOPHOR FORMULATIONS

The formulation prepared in Example 1 was divided into three parts. Each part was adjusted to a desired pH unit. The first part was adjusted to a pH of about 2.15, the second part was not adjusted for pH, the measured pH was about 2.4, and the third part was adjusted to a pH of about 4.1. All three parts were evaluated for bactericidal characteristics against target micro-organisms, namely *Staphylococcus aureus, pseudomonas aeruginosa, Candida albicans* and *Escherichia coli*. These are standard micro-organisms representing gram positives, gram negatives and fungus classifications. The bactericidal effectiveness testing procedure was conducted at several dilutions and pH to assess the bactericidal power of the formulation as follows:

10 ml of each part was added to a sterile tube. A microbial challenge of 0.1 ml containing the target microorganisms with appropriate count was added to each part. At exposure times of 1 and 5 minutes, a 1.0 ml of each inoculated dilution was transferred to a robe containing 9.0 ml of Difco Dey Engley neutralizing broth. Subsequent 1.0 ml samples of each dilution in neutralizing broth were further diluted into 9.0 ml of Difco Dey Engley neutralizing broth base. The procedure was performed at full strength and at dilutions of 1:10 and 1:100. All samples were incubated at about 30° C. for about 48 hours.

Nutrient agar pour plates were prepared for each sample and examined for the presence of colonies after a minimum of 48 hours. The results of the effectiveness testing are reported in Table 1.

TABLE 1

BACTERICIDAL EFFICACY OF NON-AQUEOUS IODOPHOR FORMULATIONS
(Kill Time in Minutes)

| Organism | Dilution | pH 2.15 | pH 2.4 | pH 4.1 |
|---|---|---|---|---|
| Staphylococcus aureus | FS | 1 | 5 | POS |
| Challenge: $1 \times 10^7$ CFU | 1:10 | 1 | 1 | POS |
| | 1:100 | 5 | 1 | 1 |
| Pseudomonas aeruginosa | FS | 1 | POS | 1 |
| Challenge: $1 \times 10^7$ CFU | 1:10 | 1 | 1 | 1 |
| | 1:100 | 1 | 1 | 1 |
| Escherichia Coli | FS | 5 | POS | 1 |
| Challenge: $2 \times 10^8$ CFU | 1:10 | 1 | 1 | 1 |
| | 1:100 | 1 | 1 | 1 |
| Candida Albicans | FS | 5 | 1 | 1 |
| Challenge: $2 \times 10^6$ CFU | 1:10 | 1 | 1 | 1 |
| | 1:100 | 1 | 1 | 1 |

Note:
FS = Full Strength
POS = Not killed in 5 minutes

The data indicates that the antimicrobial effectiveness decreases as the pH increases and all formulations become effective when diluted with water (in Difco Dey Engley broth). Overall, the antimicrobial efficacy of these formulations, is acceptable. The data confirms that the desirable pH range of the formulation is between about 2.0 to about 3.5.

EXAMPLE 3

ZONES OF INHIBITION TESTING

The antimicrobial effectiveness of the composition at pH 2.4 from Examples 1 and 2 was further tested by the zone of inhibition technique. The following procedure was followed for this test.

Nutrient plates were seeded with overnight cultures to produce confluent growth. A hole approximately 6 mm in diameter was made in the seeded agar in the center and filled with the pH 2.4 composition. The plate was incubated at 30° C. to 35° C. for a minimum of 48 hours and examined for zones of clearing around the hole (area with no growth). The radius of clear zones was measured from the hole to the edge of no growth. The results of this test are reported in Table 2.

TABLE 2

| Organism | Radius of Clear Zone (mm) |
|---|---|
| Staphylococcus aureus | 15 |
| Pseudomonas aeruginosa | 19 |
| Escherichia coli | 9 |
| Candida albicans | 13 |

These results indicate that the formulation at pH 2.4 is effective and produces large zones of inhibition.

EXAMPLE 4

STABILITY TESTING

The compositions at pH 2.15 and pH 4.10 from Examples 1 and 2 were stored in glass bottles at 60° C. for 5 months. At the completion of the aging period, the assay for iodine was made and compared with assay values of iodine before the product was put into aging. The results are reported in Table 3.

TABLE 3

| | % Available Iodine | |
|---|---|---|
| Aging Period | Composition pH 2.15 | Composition pH 4.10 |
| 0 month | 1.28 | 1.25 |
| 1 month | 1.25 | 1.22 |
| 3 month | 1.21 | 1.20 |
| 5 month | 1.23 | 1.15 |

The data indicates that the formulations of the present invention are extremely stable. Further, the composition at pH 4.10 ages at a slightly faster rate than the composition at pH 2.15. This is expected as it is known that the conversion of iodine into iodide accelerates at higher pH values.

EXAMPLE 5

BIOCOMPATIBILITY EVALUATION OF NON AQUEOUS IODOPHOR FORMULATIONS

The composition at pH 2.4 from Examples 1 and 2 were evaluated for biocompatibility by testing for primary skin irritation, closed patch skin sensitization, vaginal mucosal irritation and eye irritation as follows:

a. Primary Skin Irritation:

Healthy, female New Zealand rabbits' backs were clipped free of hair. Two sites were chosen on each rabbit, with skin left intact on one site and skin abraded on the other site. 0.5 ml of the formulation was applied to the test site, covered with gauze, and wrapped with an occlusive binder. After 24 hours, the binder was removed and an evaluation of the skin for erythema and edema was performed. A subsequent evaluation was performed, after 72 hours post application. The results after 24 and 72 hours is reported in Table 4. A total of six New Zealand White Rabbits were used in this evaluation. The primary irritation index was determined to be zero indicating that the solution was non-irritating.

TABLE 4

| | | DERMAL REACTION | | | |
|---|---|---|---|---|---|
| | | 24 Hours | | 72 Hours | |
| Rabbit Tag Number | Skin Reaction | Abraded | Intact | Abraded | Intact |
| 7106 | Erythema | 0 | 0 | 0 | 0 |
| | Edema | 0 | 0 | 0 | 0 |
| 7107 | Erythema | 0 | 0 | 0 | 0 |
| | Edema | 0 | 0 | 0 | 0 |
| 7108 | Erythema | 0 | 0 | 0 | 0 |
| | Edema | 0 | 0 | 0 | 0 |
| 7109 | Erythema | 0 | 0 | 0 | 0 |
| | Edema | 0 | 0 | 0 | 0 |
| 7110 | Erythema | 0 | 0 | 0 | 0 |
| | Edema | 0 | 0 | 0 | 0 |
| 7111 | Erythema | 0 | 0 | 0 | 0 |
| | Edema | 0 | 0 | 0 | 0 |

EVALUATION OF SKIN REACTION

| Erythema and Eschar Formation | Value | Edema Formation | Value |
|---|---|---|---|
| No erythema | 0 | No edema | 0 |
| Very slight erythema (barely perceptible) | 1 | Very slight edema (barely perceptible) | 1 |
| Well-defined erythema | 2 | Slight edema (edges of area well defined by definite raising) | 2 |
| Moderate to severe erythema | 3 | Moderate edema (raised approximately 1 millimeter) | 3 |
| Severe erythema (beet redness to slight eschar formation injuries in depth) | 4 | Severe edema (raised more than 1 millimeter and extending beyond the area of exposure) | 4 |

| INDEX | EVALUATION |
|---|---|
| 0.00 | No irritation |
| 0.01–0.99 | Irritation barely perceptible |
| 1.00–1.99 | Slight irritation |
| 2.00–2.99 | Mild irritation |
| 3.00–5.99 | Moderate irritation |
| 6.00–8.00 | Severe irritation |

*Total of 48 individual scores =
Primary Irritation Index for erythema and edma
24

0/24 = 0 b. Closed Patch Skin Sensitization:

Twenty Hartley Albino Guinea Pigs were used in this study. Prior to each induction, the upper flank skin of the guinea pig was shaved. On day zero, 0.4 ml of the formulation was placed on a hilltop chamber and placed on each animal's back. The chamber was covered with a piece of plastic and the animal's trunk was securely wrapped with elastic tape. This procedure was repeated for each of the 15 test animals. After a six hour contact period, the binders were removed.

Inductions two and three were conducted on days seven and fourteen, using the same procedure. After induction three, the animals were rested for two weeks. At the termination of this period, the opposite upper flank of the fifteen induced animals and five naive control animals were shaved. Following the same procedure (for induction), a challenge application (6-hour contact) was done for each test and control animals.

Following the challenge application, observations of the test and control sites were done at 24 and 48 hours post application. The sites were examined for erythema and edema, using the Draize method of scoring to grade reactions. Severity and incidence of reactions in the test and control groups were calculated. The incidence and severity scores were zero for both indicating that the solution is a non-sensitizer. The results are reported in Tables 5, 6, 7 and 8.

$$\text{Incidence} = \frac{\text{\# of animals with scores} \geq 1 \text{ at either observation}}{\text{Total \# of animals}}$$

$$\text{Severity} = \frac{\text{Arithmetic total of all scores}}{\text{Total \# of all animals}}$$

TABLE 5

EVALUATION OF SKIN REACTIONS

| Erythema and Eschar Formation | Value |
|---|---|
| No erythema | 0 |
| Very faint erythema, non-confluent | 0.5 |
| Very slight erythema, barely perceptible | 1 |
| Well-defined, moderate erythema | 2 |
| Moderate to severe erythema, with or without edema | 3 |

TABLE 6

TEST GROUP

| Animal Number | Erythema 24 Hour | Score 48 Hour |
|---|---|---|
| 3611 | 0 | 0 |
| 3612 | 0 | 0 |
| 3613 | 0 | 0 |
| 3614 | 0 | 0 |
| 3615 | 0 | 0 |
| 3616 | 0 | 0 |
| 3617 | 0 | 0 |
| 3618 | 0 | 0 |
| 3619 | 0 | 0 |
| 3620 | 0 | 0 |
| 3621 | 0 | 0 |
| 3622 | 0 | 0 |
| 3623 | 0 | 0 |
| 3624 | 0 | 0 |
| 3625 | 0 | 0 |

TABLE 7

NAIVE CONTROL GROUP

| Animal Number | Erythema 24 Hour | Score 48 Hour |
|---|---|---|
| 3626 | 0 | 0 |
| 3627 | 0 | 0 |
| 3628 | 0 | 0 |
| 3629 | 0 | 0 |
| 3630 | 0 | 0 |

TABLE 8

INCIDENCE AND SEVERITY INDICES

| Test Group: | Incidence = 0/15 = 0 |
|---|---|
|  | Severity = 0/15 = 0 |
| Control Group: | Incidence = 0/5 = 0 |
|  | Severity = 0/5 = 0 | c. Vaginal Mucosal Irritation:

Six New Zealand White Rabbits were used in this study. Approximately 1.0 ml of the formulation was applied to each of the three adult female rabbits to coat the vaginal tract. Concurrent negative controls (0.9% sodium chloride for injection, USP) were also used to dose three rabbits. After a dosing regimen of five days, the animals were euthanized twenty hours after the last dose. The vagina from each animal was dissected and fixed in 10% formalin solution. The tissues were examined after hematoxylin and eosin staining. The results are reported in Table 9. Slight erythema was noted in the vaginal tract of all the test rabbits. No abnormalities were observed among the control animals. Based on the histopathology, the solution passed the vaginal mucosal irritation test.

TABLE 9

VAGINAL MUCOSA IRRITATION TEST

| | Control | | | | | | | | | Biomat No. 920800A | | | | | | | | |
|---|---|---|---|---|---|---|---|---|---|---|---|---|---|---|---|---|---|---|
| | 7226 | | | 7227 | | | 7228 | | | 7211 | | | 7220 | | | 7222 | | |
| | Ant | Mid | Pos | Ant | Mid | Pos | Ant | Mid | Pos | Ant | Mid | Pos | Ant | Mid | Pos | Ant | Mid | Pos |
| Vaginal Tissue Lumen Exudate Epithelium | X | | | | | | | | | 1 | 1 | 1 | | | | | | |
| Leukocytic Infiltration Intraepithelial Cyst Erosion | | P | | | P | | 1 | 1 | 2 | 1 | 1 | 1 | | 1 | 1 | 1 | | 1 |
| Lamina Propria Leukocytic Infiltration | | 1 | 1 | 1 | 1 | 1 | 2 | 2 | 3 | 1 | 1 | 1 | 1 | 2 | 1 | 2 | 1 | 1 |
| Edema | 1 | | | 1 | 1 | | 1 | 2 | | 1 | 1 | | 2 | | 1 | 2 | | |
| Hemorrhage, Focal Congestion | | | | | | | | | | | 1 | | | 2 | 2 | 2 | 1 |

Key:
Ant = Anterior
Mid = Middle
Pos = Posterior
X = Not Remarkable
N = No Section
1 = Minimal
2 = Slight/Mild
3 = Moderate
4 = Moderately Severe
5 = Severe/High d. Eye Irritation:

Six New Zealand Albino Rabbits, free from evidence of ocular irritation and corneal abnormalities, were used in this study. Approximately 0.1 ml of the formulation was placed into the conjunctival sac of one eye of each rabbit. The eyes were not washed. The eyes were examined and scored by the Draize technique on days 1, 2, and 3. The primary eye irritation score for each rabbit, each day, was calculated. The results are reported in Table 10. Based on the results, the solution was considered to be a non-irritant to the eyes as defined in 16 CFR 1500.42.

TABLE 10

| An. #/Sex: | Item | Tissue | Reading | Day: 1 | Day: 2 | Day: 3 |
|---|---|---|---|---|---|---|
| D4677-M | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: | | A | A | A |

TABLE 10-continued

| An. #/Sex: | Item | Tissue | Reading | Day: 1 | Day: 2 | Day: 3 |
|---|---|---|---|---|---|---|
| | | Pretest Body Weight: 2.1 kg | | | | |
| D4718-F | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: | | A | A | A |
| | | Pretest Body Weight: 2.0 kg | | | | |
| D4771-F | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |

TABLE 10-continued

| An. #/Sex: | Item | Tissue | Reading | Day: 1 | 2 | 3 |
|---|---|---|---|---|---|---|
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: Pretest Body Weight: 2.6 kg | | A | A | A |
| D4777-F | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: Pretest Body Weight: 2.5 kg | | A | A | A |
| D4773-F | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: Pretest Body Weight: 2.4 kg | | A | A | A |
| D4779-F | A | Cornea | Opacity | 0 | 0 | 0 |
| | B | | Area | 0 | 0 | 0 |
| | | 1. Total = (A × B) × 5 | | 0 | 0 | 0 |
| | C | Iris | | 0 | 0 | 0 |
| | | 2. Total = C × 5 | | 0 | 0 | 0 |
| | D | Conjunctive | Redness | 1 | 0 | 0 |
| | E | | Chemosis | 0 | 0 | 0 |
| | F | | Discharge | 0a | 0a | 0a |
| | | 3. Total = (D + E + F) × 2 | | 2 | 0 | 0 |
| | | Totals = 1 + 2 + 3 | | 2 | 0 | 0 |
| | | Systemic Observations: Pretest Body Weight: 2.7 kg | | A | A | A |

Key: A = normal
a = fur around treated eye stained yellow

SCALE FOR SCORING OCULAR LESIONS**

(1) Cornea
  (A) Opacity-degree of density (area most dense taken for reading)

| | |
|---|---|
| No opacity | 0 |
| Scattered or diffuse area, details of iris clearly visible | 1* |
| Easily discernible translucent areas, details of iris slightly obscured | 2* |
| Opalescent areas, no details of iris visible, size of pupil barely discernible | 3* |
| Opaque, iris invisible | 4* |

(B) Area of cornea involved

| | |
|---|---|
| One quarter (or less) but not zero | 1 |
| Greater than one quarter, but less than half | 2 |
| Greater than half, but less than three quarters | 3 |
| Greater than three quarters, up to whole area | 4 |

SCORE EQUALS A × B × 5    Total Maximum = 80

(2) IRIS
  (A) Values

| | |
|---|---|
| Normal | 0 |
| Folds above normal, congestion, swelling, circumcorneal injection (any or all of these or combination of any thereof) iris still reacting to light (sluggish reaction is positive) | 1* |
| No reaction to light, hemorrhage, gross destruction (any or all of these) | 2* |

SCORE EQUALS A × 5    Total Maximum = 10

(3) CONJUNCTIVAE
  (A) Redness (refers to palperal and bulbar conjunctivae excluding cornea & iris)

| | |
|---|---|
| Vessels normal | 0 |
| Vessels definitely injected above normal | 1 |
| More diffuse, deeper crimson red, individual vessels not easily discernible | 2* |
| Diffuse beefy red | 3* |

(B) Chemosis

| | |
|---|---|
| No swelling | 0 |
| Any swelling above normal (includes nictitating membrane) | 1 |
| Obvious swelling with partial eversion of lids | 2* |
| Swelling with lids about half closed | 3* |
| Swelling with lids about half closed to completely closed | 4* |

(C) Discharge

| | |
|---|---|
| No discharge | 0 |
| Any amount different from normal (does not include small amounts observed in inner canthus of normal animals) | 1 |
| Discharge with moistening of the lids and hairs just adjacent to lids | 2 |
| Discharge with moistening of the lids and hairs and considerable area around the eye | 3 |

SCORE EQUALS (A + B + C) × 2    Total Maximum = 20

*= An animal shall be considered as exhibiting a positive reaction
**= Draize, J. H. et al., J. Pharm. Exp. Ther. 82:377–390, 1994

The maximum total score is the sum of all scores obtained for the cornea, iris and conjunctivae. Total maximum scores possible=110

CONCLUSION

| | |
|---|---|
| Non-irritant | 0 to 1 rabbit(s) with positive scores |
| Indeterminate | 2 to 3 rabbit(s) with positive scores |
| Irritant | 4 to 6 rabbit(s) with positive scores |

EXAMPLE 5

STABILITY OF A NON-AQUEOUS FORMULATION IN A UNIT DOSE PACKAGED SURGICAL SCRUB

The stability of the unit dose surgical scrub packaged product with the formulation of the present invention was evaluated. A single dose of surgical scrub product consists of a polyethylene molded handle with soft bristles on one side to scrub the hand. The other side of the brush is glued to a polyurethane foam impregnated with scrub solution. The polyurethane foam is synthesized from a polyisocyanate, a polyglycol, a chain extender, and a blowing agent. The sponge is a polyester polyurethane or a polyether polyurethane type. The impregnated sponge brush unit is packaged in a boat type packaging sealed on the top using the lidding stock. Both the boat and the lidding stock materials are manufactured using a combination of plastic materials.

The formulation of Example 1 was adjusted to pH 3.0. The unit dose package was impregnated with 10 ml of the formulation and aged at room temperature for 18 months. The results of the study are reported in Table 11. The E-Z SCRUB® Surgical Scrub System with povidone iodine 1.0% (brush/sponge), Order No. 372013 (a trademark of Becton, Dickinson and Company, Franklin Lakes, N.J.).

The zero time iodine concentration was obtained by titrating the bulk solution before impregnating the polyether polyurethane sponge. There was an initial drop of iodine due to complexation with the polyurethane sponge. After the initial drop, there was no degradation of iodine due to aging up to 18 months. There was no gradual decrease in the weight of packaging indicating that there was no weight loss. At each test interval when the packages were opened, the contents were found to be moist. The packages had not dried as generally is the case with water based surgical scrub products.

TABLE 11

% Available Iodine and Water Moisture Loss In A Unit Dose Packaged Surgical Scrub

| Aging Period (months) | Percent Available Iodine | % of moisture loss in Sealed Package |
|---|---|---|
| 0 | 1.39 | — |
| 3 | 1.27 | no loss |
| 6 | 1.33 | no loss |
| 12 | 1.32 | no loss |
| 18 | 1.26 | no loss |

TABLE 12

% Available Iodine and Water Moisture Loss of the E-Z SCRUB ® Surgical Scrub System, Order No. 372013

| Aging Period (months) | Percent Available Iodine | % of moisture loss in Sealed Package |
|---|---|---|
| 0 | 1.8 | — |
| 3 | 1.7 | 5.1 |
| 6 | 2.2 | 13.5 |
| 12 | 2.5 | 17.3 |
| 18 | 2.7 | 19.7 |

What is claimed is:

1. An emollient, non-aqueous iodophor formulation comprising:

(a) a non-ionic pluronic surfactant containing 50–70% ethylene oxide in amount from about 10 to 20 weight percent of the total composition;

(b) a nonylphenoxypolyethyleneoxy ethanol in an amount from about 10 to about 20 weight percent of the total composition;

(c) a coconut oil diethanolamine condensate in an amount from about 0.5 to about 2.0 weight percent of the total composition;

(d) a polyoxyethylene 4 lauryl ether in an amount from about 5 to about 15 weight percent of the total composition;

(e) an ethoxylated lanolin in an amount from about 1 to about 5 weight percent of the total composition;

(f) an alkylaryl sulfonate in an amount from about 1 to about 5 weight percent of the total composition;

(g) a mineral oil in an amount from about 1 to about 5 weight percent of the total composition;

(h) iodine crystals in an amount from about 0.5 to about 2.5 weight percent of the total composition;

(i) sodium iodide in an amount from about 0.5 to about 2.0 weight percent of the total composition;

(j) aloe vera in an amount from about 0.1 to about 2.0 weight percent of the total composition; and (k) propylene glycol in an amount from about 18.0 to about 70.0 weight percent of the total composition.

2. The formulation of claim 1 further comprising:

(1) a fragrance in an amount from about 0.1 to about 1.0 weight percent of the total composition.

3. The formulation of claim 2 further comprising:

(m) vitamin E in an amount from about 0.1 to about 1.0 weight percent of the total composition.

* * * * *